United States Patent
Bailey et al.

(10) Patent No.: US 6,641,520 B2
(45) Date of Patent: Nov. 4, 2003

(54) MAGNETIC FIELD GENERATOR FOR THERAPEUTIC APPLICATIONS

(75) Inventors: Richard Bailey, Houston, TX (US); Harold R. Potts, Humble, TX (US)

(73) Assignee: Electro Magnetic Resources Corp.

( * ) Notice: Subject to any disclaimer, the term of this patent is extended or adjusted under 35 U.S.C. 154(b) by 0 days.

(21) Appl. No.: 09/772,237

(22) Filed: Jan. 29, 2001

(65) Prior Publication Data

US 2002/0103411 A1 Aug. 1, 2002

(51) Int. Cl.[7] .............................................. A61B 17/52
(52) U.S. Cl. .............................. 600/9; 600/13; 600/422; 600/427
(58) Field of Search ................................ 600/9, 10, 11, 600/12, 13, 14, 15, 410, 411, 421, 422, 427

(56) References Cited

U.S. PATENT DOCUMENTS

| | | | |
|---|---|---|---|
| 703,989 A | | 7/1902 | Burry |
| 1,418,903 A | | 6/1922 | Benson |
| 4,095,588 A | | 6/1978 | Goldman |
| 4,402,309 A | * | 9/1983 | Harrison ...................... 128/1.3 |
| 4,501,265 A | | 2/1985 | Pescatore |
| 4,527,550 A | * | 7/1985 | Ruggera et al. ............. 128/1.5 |
| 4,757,804 A | | 7/1988 | Griffith |
| 5,014,699 A | | 5/1991 | Pollack |
| 5,058,582 A | * | 10/1991 | Thaler ........................ 128/419 |
| 5,084,003 A | | 1/1992 | Susic |
| 5,131,904 A | * | 7/1992 | Markoll ........................ 600/14 |
| 5,160,591 A | | 11/1992 | Liboff |
| 5,267,939 A | * | 12/1993 | Liboff et al. .................. 600/13 |
| 5,314,400 A | * | 5/1994 | Tsyb et al. ...................... 600/9 |
| 5,344,384 A | | 9/1994 | Ostrow |
| 5,366,435 A | * | 11/1994 | Jacobson ...................... 600/13 |
| 5,437,600 A | | 8/1995 | Liboff |
| 5,453,073 A | | 9/1995 | Markoll |
| 5,518,495 A | | 5/1996 | Kolt |
| 5,550,471 A | * | 8/1996 | Feld ............................ 324/318 |
| 5,752,911 A | * | 5/1998 | Canedo et al. ................. 600/9 |
| 5,842,966 A | * | 12/1998 | Markoll ....................... 600/14 |
| 5,857,957 A | * | 1/1999 | Lin ............................... 600/13 |
| 5,997,464 A | * | 12/1999 | Blackwell ..................... 600/13 |
| 6,186,941 B1 | * | 2/2001 | Blackwell ..................... 600/13 |
| 6,194,899 B1 | * | 2/2001 | Ishihara et al. ............. 324/315 |
| 6,210,317 B1 | * | 4/2001 | Bonlie ........................... 600/9 |
| 6,231,516 B1 | * | 5/2001 | Keilman et al. ............ 600/485 |
| 6,290,638 B1 | * | 9/2001 | Canedo et al. ................. 600/9 |
| 6,317,618 B1 | * | 11/2001 | Livni et al. ................. 600/410 |
| 6,336,043 B1 | * | 1/2002 | Suzuki et al. ............... 600/409 |

FOREIGN PATENT DOCUMENTS

GB     2262043 A   *   9/1993      ............ A61N/2/00

OTHER PUBLICATIONS

Jerabek, J. and Pawluk, W., Magnetic Therapy in Eastern Europe a Review of 30 Years of Research, 1998.

Blank, Martin, Ed., Medical Benefits of Electric and Magnetic Fields: Challenges for Broader Use, *Electricity and Magnetism in Biology and Medicine, 1993*; pp. 9–11; New York, NY.

(List continued on next page.)

*Primary Examiner*—Gene Mancene
*Assistant Examiner*—Frederick C. Nicolas
(74) *Attorney, Agent, or Firm*—Bracewell & Patterson LLP

(57) ABSTRACT

A magnetic field generator for therapeutic applications develops a static or direct current (DC) magnetic field. The generator is self-contained, and also concentrates the magnetic lines of flux in a specific area. A recipient of the therapy may thus place a limb, typically a wrist or lower portion of an arm, in the area of concentrated magnetic flux of the static magnetic field.

16 Claims, 6 Drawing Sheets

OTHER PUBLICATIONS

Brighton, C.T. and Pollack, S.R., physical and Biological Principles Affecting Weak Elf Electromagnetic Bioresponses, *Electromagnetics in Biology and Medicine, 1991*; pp. 1–13; San Francisco, CA.

Pilla, Arthur A., State of the Art in Electromagnetic Therapeutics: Soft Tissue Applications, *Electricity and Magnetism in Biology and Medicine, 1999*; pp. 871–874; Plenum Publishers.

Adey, W. Ross, Horizons in Science: Physical Regulation of Living Matter as an Emergent Concept in Health and Disease, *Electricity and Magnetism in Biology and Medicine, 1999*; pp. 53–57; Plenum Publishers.

Blank, Martin, Mechanisms of Biological Interaction with Electric and Magnetic Fields, *Electricity and Magnetism in Biology and Medicine, 1999*; pp. 21–25; Plenum Publishers.

Cleary, Stephen F., Effects of Radio–Frequency Radiation on Mammalian Cells and Biomolecules in Vitro; *1995 American Chemical Society 26*; pp. 467–477.

Blank, Martin, Electric Stimulation of Protein Synthesis in Muscle; *1995 American Chemical Society 9*; pp. 143–153.

Weaver, James C. and Astumian, R. Dean, Issues Relating to Causality of Bioelectromagnetic Effects; *1995 American Chemical Society 5*; pp. 79–96.

Adey, W. Ross, A Growing Scientific Consensus on the Cell and Molecular Biology Mediating—Interactions with Environmental Electromagnetic Fields; *Biological Effects of Magnetic and Electromagnetic Fields 1996*, 4; pp. 45–62; New York, NY.

Polk, Charles, Physical Mechanisms for Biological Effects of Low Field Intensity Elf Magnetic Fields, *Biological Effects of Magnetic and Electromagnetic Fields 1996*, 5; pp. 63–83; New York, NY.

Srauer, J. J., Magnetism and the Permanent Magnet, *Advances in Permanent Magnets 1989*, pp. 15–33; New York, NY.

\* cited by examiner

MAGNETIC FIELD GENERATOR FOR THERAPEUTIC APPLICATIONS

BACKGROUND OF INVENTION

1. Field of Invention

The present invention relates to generators of static or direct current magnetic fields, especially those for therapeutic applications.

2. Description of the Prior Art

There has recently been an increased interest in therapeutic application of magnetic fields. There have also been earlier efforts of others in this area. The recent efforts, as well as those earlier made, can be categorized into three general types, based on the mechanism for generating and applying the magnetic field.

The first type were what could be generally referred to as systemic applications. These were large, tubular mechanisms which could accommodate a human body within them. A patient or recipient could thus be subjected to magnetic therapy through their entire body. These systems were large, cumbersome and relatively immobile. Examples of this type of therapeutic systems included U.S. Pat. Nos. 1,418,903; 4,095,588; 5,084,003; 5,160,591; and 5,437,600.

A second type of system was that of magnetic therapeutic applicator systems in the form of flexible panels, belts or collars, containing either electromagnets or permanent magnets. These applicator systems could be placed on or about portion of the recipient's body to allow application of the magnetic therapy. Because of their close proximity to the recipients body, considerations limited the amount and time duration of application of magnetic therapy. Examples of this type system were U.S. Pat. Nos. 4,757,804; 5,084,003 and 5,344,384.

The third type of system was that of a cylindrical or toroidal magnetic field generator, often small and portable, into which a treatment recipient could place a limb to receive electromagnetic therapy. Because of size and other limitations, the magnetic field strength generated in this type system was usually relatively low. Also, the magnetic field was a time varying one. Electrical current applied to cause the magnetic field was time varying, whether in the form of simple alternating current waveforms or a waveform composed of a series of time-spaced pulses.

SUMMARY OF INVENTION

Briefly, the present invention provides a new and improved magnetic field generator for therapeutic applications. A magnetic field generator according to the present invention provides therapeutic application of a static magnetic field to a recipient. Magnetic field generators according to the present invention include a magnetic field generating coil in the form of a wound wire coil. A mounting member has the coil mounted on it. The mounting member also has an opening formed through it, the opening being of a size to permit insertion of a therapy recipient's limb.

The magnetic field generator according to the present invention includes an electrical power supply which furnishes current to the magnetic field generating coil. Flow of current in the magnetic field generating coil causes a static electromagnetic field to occur within the opening of the mounting member for application to the recipient's limb.

The magnetic field generator according to the present invention also includes a control circuit which regulates the amount of current flowing in the electromagnetic field generating coil. The control circuit permits adjustable regulation or control of the electromagnetic field strength generated by the field generating coil. The control circuit permits an operator to establish a desired field strength and then regulates the amount of power available to the field generating coil to achieve the established field strength.

The field generating coil of the present invention is of a size and capacity to generate substantial static electromagnetic fields, such as up to a range of around 4000 gauss. A cooling system is provided with the magnetic field generator to remove heat during operation of the field generating coil.

The magnetic field generator is also provided with shielding externally of the field generating coil and the mounting member. The magnetic field generator is also enclosed in a housing which has an access passage for insertion of a recipient's limb into the opening of the mounting member. The housing is mounted on a transport carriage which supports the magnetic field generator, while allowing ease of movement of the magnetic field generator from place to place.

DESCRIPTION OF THE PREFERRED EMBODIMENT

Figure 1:
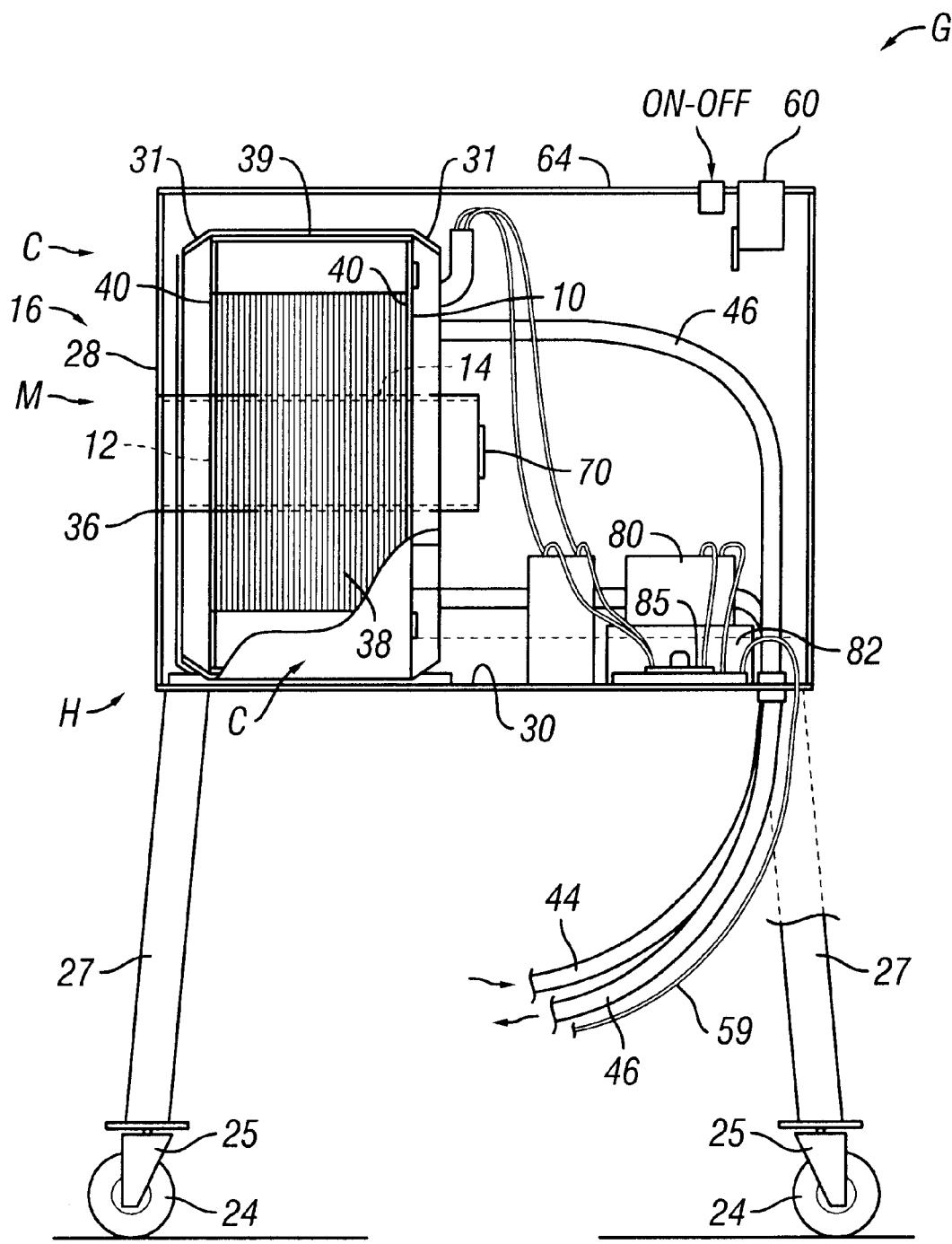
FIG. 1 is a side elevation view, taken partly in cross-section, of a magnetic field generator according to the present invention.

In the drawings, the letter G designates generally a self-contained magnetic field generator according to the present invention. The magnetic field generator G is intended for therapeutic applications, developing and concentrating a static or DC electro-magnetic field. The magnetic field generator G permits the magnetic lines of flux to be concentrated in a specific area where a recipient of therapy may place a limb or limb portion, usually a lower arm portion or wrist of a recipient, to receive therapy. It should also be understood that an ankle or lower leg portion may also inserted and treated, as well. The magnetic field generator is designed for continuous or intermittent application of static electromagnetic fields for fixed time intervals of minutes as contrasted to application of a number of closely time-spaced pulses. The strength of the static magnetic field generated can be varied according to therapeutic needs and can be as high as approximately 4000 Gauss, or 0.40 Tesla.

The magnetic field generator G according to the present invention includes a magnetic field generating coil C in the form of a wound wire coil. The coil C is located about a generally tubular mounting member M in the form of a spool 10. The mounting member M has an opening or passage 12 formed in a longitudinal central portion 14 to allow insertion of a recipient's limb or limb portion. This is typically done by insertion of a hand so that a wrist or lower arm is located centrally within the coil C to receive the electro-magnetic field generated by the coil C.

Figure 5:
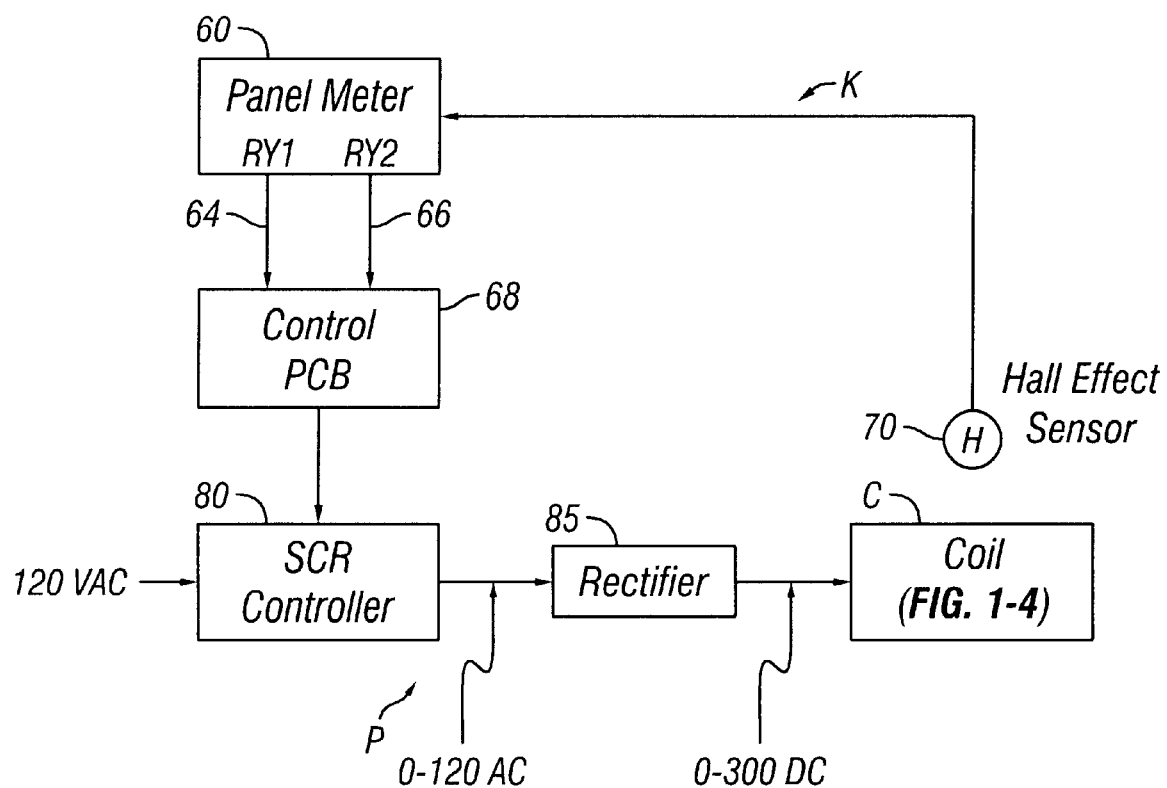
FIG. 5 is a schematic electrical circuit diagram of electrical components of the magnetic field generator of FIG. 1.
Figure 6:
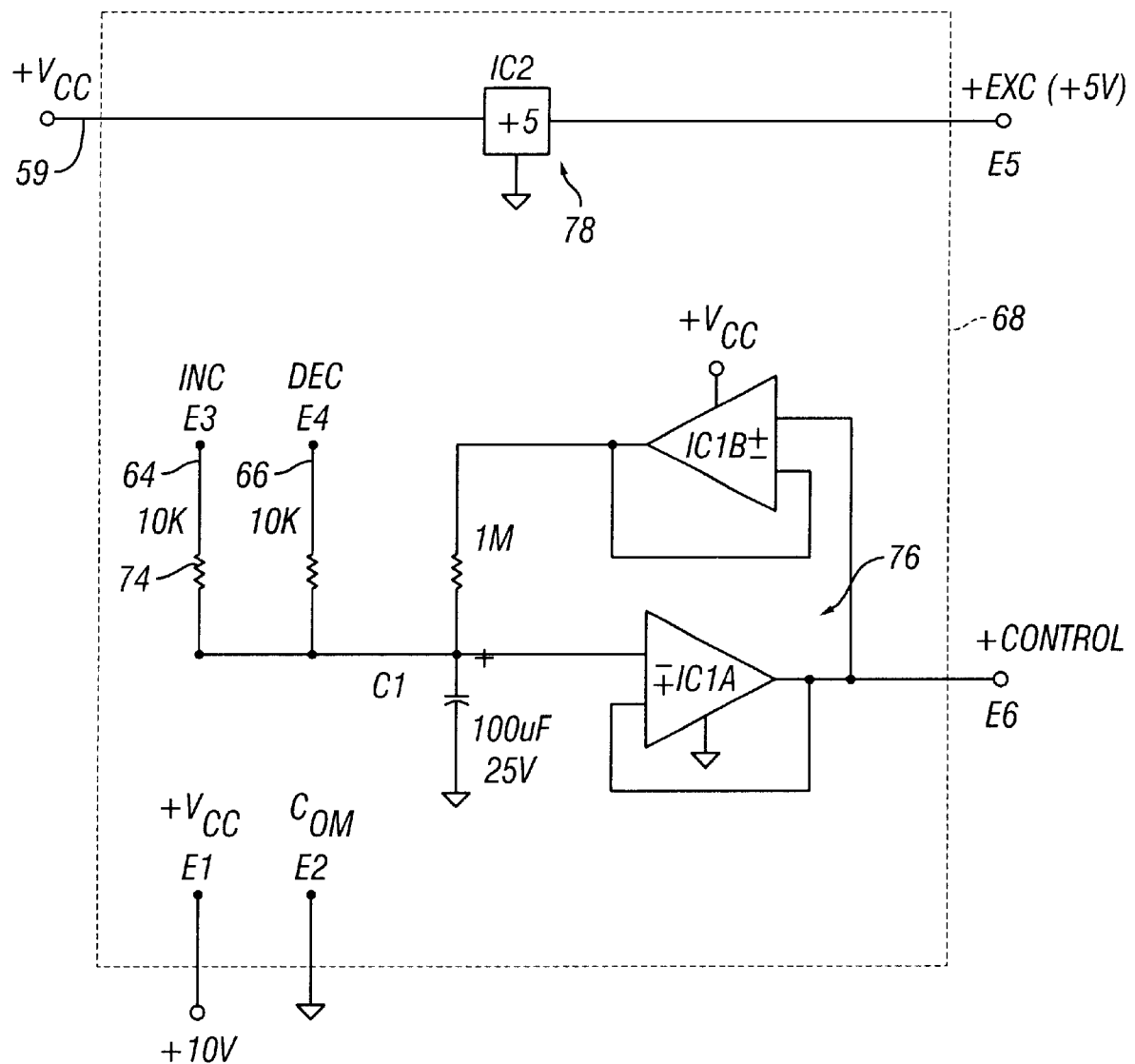
FIG. 6 is a schematic electrical circuit diagram of the control portions of the circuit of FIG. 5.
Figure 7:
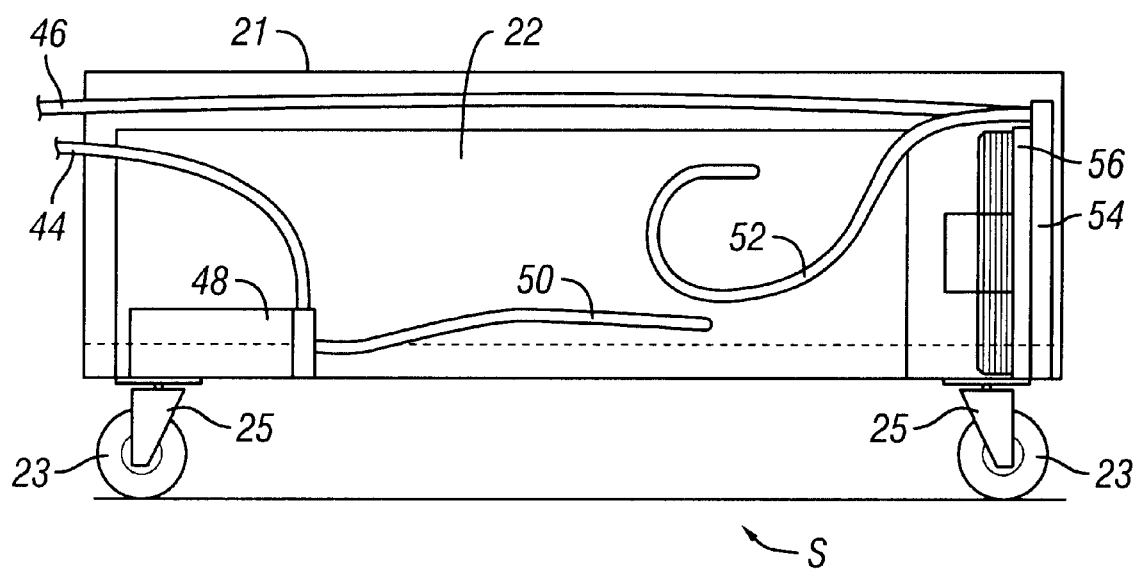
FIG. 7 is a schematic diagram of the coolant unit for the magnetic field generator of FIG. 1.

The magnetic field generator G also includes a power supply circuit P (FIG. 5) which furnishes current to the coil C and causes the coil to generate a static or DC electromagnetic field within the opening 12 of mounting member M for application to the recipient's limb located therein. The magnetic field generator G also includes a control circuit K (FIGS. 5 & 6) which forms the direct current and regulates the amount of such current flowing to the magnetic coil C to control the intensity of the magnetic field generated. According to the present invention, a cooling system S (FIG. 7) is also provided to remove excess heat from the magnetic coil C and other portions of the generator G.

Figure 2:
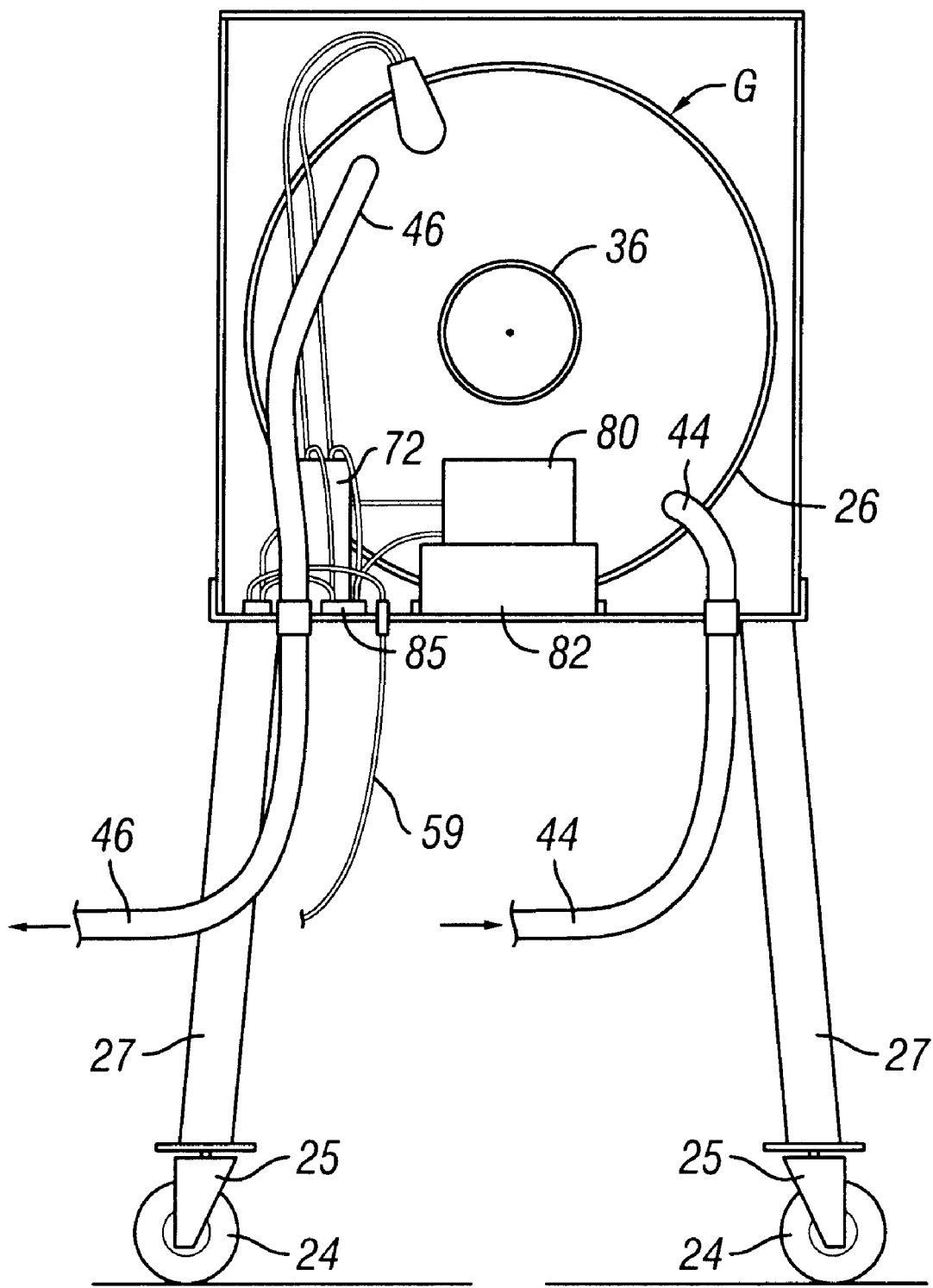
FIG. 2 is a front elevation view, taken partly in cross-section, of the magnetic field generator of FIG. 1.
Figure 3:
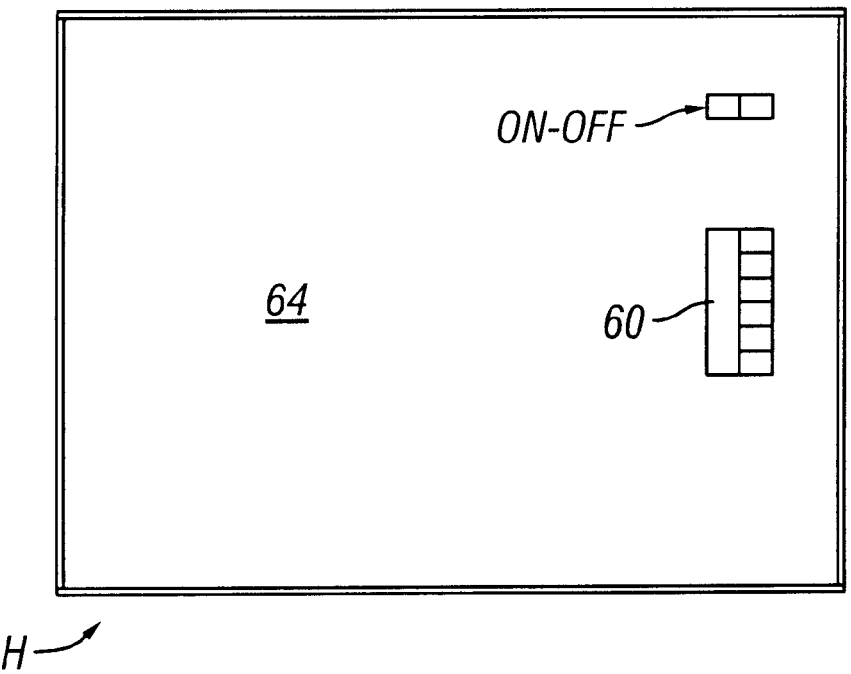
FIG. 3 is a top view of the magnetic field generator of FIG. 1.
Figure 4:
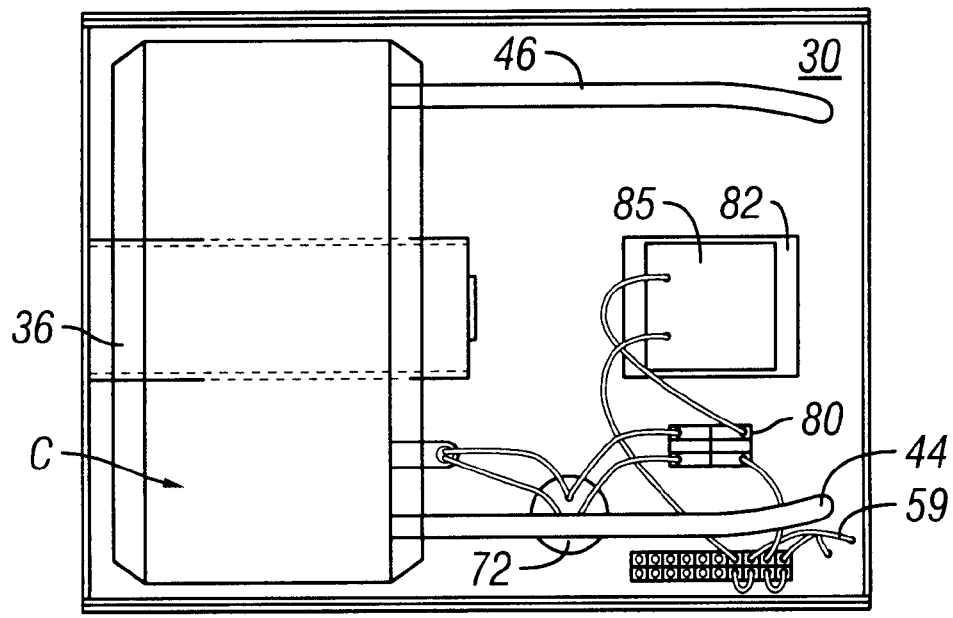
FIG. 4 is a top view of one magnetic field generator of FIGS. 1 and 3 with the top cover removed.

The magnetic field generator G is contained within a housing H (FIGS. 1–3) of stainless steel or other suitable material. The housing H includes a cabinet or chamber 16 which contains the power supply circuit P and the control circuit K. The housing H is mounted for movement on wheels 24 rotatably mounted in fixed or rotatable yokes or wheel attachment members 25 on legs 27 beneath each of four lower corner portions of the cabinet 16.

The magnetic coil C is mounted in a cylindrical or toroidal shaped magnetic shield enclosure or cover 26 formed of a suitable magnetic shielding material, such as a high permeability steel alloy to substantially confine the electromagnetic lines of flux from the coil C to the general area of the opening 12. Preferably, the steel alloy of the shield 26 should have a relative ($\mu_r$) permeability of 1800 or more. Such materials are available from a number of commercial sources. The shield cover 26 is located within the housing H behind a front face 28 of cabinet 16 on a floor or support surface 30 of the cabinet 16. The magnetic shield cover 26 has a central port or opening 34 into which a receptor sleeve 36 is fitted. The receptor sleeve 36 is located within the longitudinal central passage 14 of the spool 10 of the mounting member M, defining the opening 12 into which the recipient inserts a limb portion for treatment. The enclosure 26 also includes an inwardly tapering coil or housing 31 at each end to further confine the electromagnetic lines of flux.

The electro-magnetic coil C is of an air core solenoid type. In the preferred embodiment, the coil C is formed of approximately 3100 turns 38 of #12AWG copper wire wrapped on the spool or bobbin 10, which is formed of a suitable strength polycarbonate synthetic resin or plastic. The opening or aperture 12 in the spool 10 is about six inches in internal diameter along its longitudinal axis. End collars 40 of spool 10 are about twenty-one inches in diameter, and the spool 10 is about nine inches in width. The coil windings 38 are enclosed within a plastic cylinder and immersed in silicon based transformer oil to facilitate heat transfer from the magnet coil C. The DC resistance of the copper wire windings 38 of coil C is approximately 10 ohms. With 170 VDC applied, 17 amperes are drawn when the coil C fully energized. The resultant field strength of the resulting static or DC electromagnetic field is approximately 4000 gauss or 0.40 Tesla.

When producing field intensities of strengths of up to 0.40 Tesla, significant heat is generated. The cooling system S is provided to remove excess heat from the generator G and to facilitate cooling. The cooling system S is mounted in a coolant distribution unit U (FIG. 7). the cooling distribution unit U is supported in a housing 21 separately movable from the support for movement on wheels 23 rotatably mounted in fixed or rotatable yokes 25 or other wheel support and attachment members. The cooling system S is a closed loop system which contains a supply of a suitable heat exchange or coolant fluid, such as a silicone-based oil, stored in reservoir 22. The magnetic shield cover 26 for coil C is a fluid-tight housing, connected to an inlet conduit 44 and an outlet conduit 46 of the cooling system S. The coolant fluid is moved through the cooling system S to the coil enclosure 26 by a pump 48 connected to reservoir 22 by a conduit 50. Fluid stored in reservoir 22 is provided by conduit 52 from a heat exchanger 54. The coolant fluid in the heat exchanger 54 is cooled by air moved by a fan 56. After cooling, the coolant fluid flows through the conduit 52 to the reservoir 22. Fluid from the coil enclosure 26 is transported by the conduit 46 to the heat exchanger 54 and moves under forces imparted by the pump 48 to the closed loop system S.

The power supply circuit P (FIG. 5) develops the required adjustable level of DC voltages from conventional AC line 120 voltage input 59 to provide power at levels required by the magnet coil C. The power supply P also provides operating power for operation of electronic components of the control circuit K. The output of the power supply circuit for coil C is regulated to a level established an operator based on an input level control mechanism in the form of a panel meter 60 on a removable top cover 64 (FIG. 3) of housing H.

The panel meter 60 is a conventional, commercially available unit such as one provided as P/N 500-218 by Electro-Numerics, Inc. of Temecula, Calif. The panel meter 60 provides basic control of the generator G and also furnishes a display of the field strength as well as set points for the desired static magnetic field strength output for the generator G. The panel meter 60 provides control signals that increase or decrease the magnetic strength. Output signals on conductors 64 and 66 from panel meter 60 are provided to a controller printed circuit board 68 (FIG. 6) that converts the signals furnished it to a signal at a level from 0 to 10 volts required for operation of the control circuit K. The output signal on conductor 64 is present at a level of 10 volts whenever the measured field strength as determined by a Hall effect sensor 70 is below the desired operator setting. The signal on the conductor 64 is used to indicate a need exists for increasing the magnetic field strength. Conversely, a signal is present on conductor 66 at a level of 0 volts when the measured field strength detected by the Hall effect sensor 70 exceeds the operator established level and a need thus exists to reduce the field strength. The Hall effect sensor 70 connected to the panel meter 60 is mounted in housing 26 to monitor the field strength or gauss level output of the generator G.

The controller printed circuit board 68 accepts the 10 volt signal from conductor 64 and the 0 volt signal from conductor 66 which are converted to a control signal having a voltage level varying from 0 to 10 volts DC. The output signal so provided by the controller printed circuit board 68 is proportional to the time the signals are active on conductors 64 and 66. When the signal on conductor 64 is present, a capacitor 72 (FIG. 6) of controller printed circuit board 68 is charged through a resistor 74. The capacitor 72 is connected to an input of an operational amplifier 76 which is configured as a voltage follower and presents a high impedance input and output at a gain of 1. A dual op amp (Harris LM358) integrated circuit 78 on the printed circuit board 68 insures the charge on the capacitor 72 remains constant after the signal on conductor 64 is removed, indicating that the desired field strength level has been achieved by the generator G. The output voltage from operational amplifier 76 is governed by the charge on capacitor 72 and is applied as a control input to an SCR controller 80. The voltage range of the output from the controller printed circuit board 68, as has been noted is from 0 volts to 10 volts DC, corresponding to an output range of from 0 to 100% output from the SCR controller 80.

The SCR controller 80 is a commercially available unit, such as an EP-1 available from Phasetronics, Inc. of Clearwater, Fla. The SCR controller 80 receives the DC control signal formed by the controller printed circuit board 68 and provides an output voltage of from 0 to 120 RMS, alternating current, depending upon the magnitude of the control signal furnished. The output voltage from the SCR controller 80 is furnished to a step-up transformer 82, normally at a 0:2 ratio to double the voltage furnished to a rectifier 85.

The rectifier 85 converts the alternating current power output level from the SCR controller 80 to a direct current voltage output level. Preferably, the rectifier assembly 85 is in the form of a conventional bridge rectifier with a capacitor to provide capacity filtering. Based on the amount of power furnished by the rectifier assembly 85, the generator G forms static magnetic fields of desired strength in the manner set forth above. Further, based on the field strength readings obtained from the Hall effect sensor 70, the control circuit K adjusts the magnetic field strength to insure that the field strength remains within the levels established by the operator.

The control circuit K (FIG. 5) thus performs the control and monitoring functions for the generator G. The magnetic field strength is monitored by the sensor 70 mounted near the magnet coil assembly C. Signals are provided from the magnetic field sensor 70 are monitored in the control circuit K to regulate the power applied to the magnet coil C and thus control the actual field strength of the magnet coil C. If desired, the coil temperature may be monitored for safety reasons, and should the temperature of the magnetic coil C exceed established limits the magnet is powered off until the temperature returns to normal levels. The generator G may also use a countdown timer to control the operating treatment time or "on time" of the magnetic coil C during treatment of a therapy recipient.

The foregoing disclosure and description of the invention are illustrative and explanatory thereof, and various changes in the size, shape, materials, components, circuit elements, wiring connections and contacts, as well as in the details of the illustrated circuitry and construction and method of operation may be made without departing from the spirit of the invention.

What is claimed is:

1. A magnetic field generator for therapeutic application of a static magnetic field to a recipient, comprising:
    a magnetic field generating coil composed of a wound wire coil generating the static magnetic field in response to electrical power;
    a mounting member having the coil mounted thereon and having an opening therethrough of a size to permit insertion of a limb of the recipient in order to receive electromagnetic therapy from the magnetic field coil;
    an electrical power supply furnishing power to the magnetic field coil to cause the coil to generate a static electromagnetic field within the opening of the mounting member for application to the recipient's limb;
    a level control mechanism providing a reference signal representing a specified electro-magnetic field strength set point for regulating the power furnished to the magnetic field coil;
    a field strength sensor detecting the static electromagnetic field strength generated by the magnetic field coil and forming a field strength signal representing the detected electro-magnetic field strength in the opening in the mounting member;
    a control signal generator receiving the field strength signal from the field strength sensor and the reference signal from the level control mechanism representing a specified electro-magnetic field strength set point; and
    the control signal generator forming a signal to regulate the power flowing from the electrical power supply to the magnetic field coil.

2. The magnetic field generator of claim 1, wherein the mounting member comprises:
    a spool member having a tubular body with a central tubular passage therethrough forming the opening to permit insertion of the limb of the recipient.

3. The magnetic field generator of claim 1, further including:
    a magnetic shield member enclosing the magnetic field generating coil and the mounting member.

4. The magnetic field generator of claim 1, further including:
    a cooling system for removing excess heat from the magnetic field generating coil.

5. The magnetic field generator of claim 4, wherein the cooling system comprises:
    a supply of coolant fluid;
    a conduit system circulating the coolant fluid between the coolant fluid supply and the magnetic field generating coil;
    a pump moving the coolant fluid through the conduit system;
    a heat exchanger connected to the conduit system for removing heat from the coolant fluid.

6. The magnetic field generator of claim 1, wherein the magnetic field generating coil generates a static magnetic field ranging in strength from 0 to 4,000 gauss based on the power furnished by the electrical power supply.

7. The magnetic field generator of claim 1, further including:
    a housing enclosing the magnetic field generator, said housing having an access passage for inserting a recipient's limb into the opening of the mounting member; and
    a transport carriage supporting the housing for movement of the magnetic field generator.

8. The magnetic field generator of claim 1, further including:
    a controller responding to the signal from the control signal generator and providing an output voltage based on the magnitude of the signal from the control signal generator.

9. The magnetic field generator of claim 1, further including:
    a rectifier converting the output voltage of the controller to direct current output power and providing the direct current output power to the magnetic field generating coil.

10. The magnetic field generator of claim 1, wherein the field strength sensor is mounted with the mounting member.

11. The magnetic field generator of claim 7, wherein the field strength sensor is mounted in the housing.

12. The magnetic field generator of claim 7, wherein the field strength sensor is mounted with the mounting member.

13. The magnetic field generator of claim 7, wherein the field strength sensor is a Hall effect sensor.

14. A magnetic field generator for therapeutic application of a static magnetic field to a recipient, comprising:

- a magnetic field generating coil composed of a wound wire coil, said coil forming a static magnetic field in response to flow of power thereto;
- a mounting member having the coil mounted thereon and having an opening therethrough of a size to permit insertion of a limb of the recipient in order to receive electromagnetic therapy from the magnetic field coil;
- a level control mechanism providing a reference signal for regulating the power furnished to the magnetic field coil;
- a field strength sensor detecting the static electromagnetic field strength generated in the opening in the mounting member by the magnetic field coil and forming a field strength signal representing the detected static electromagnetic field strength;
- a control signal generator receiving the field strength signal from the field strength sensor and the reference signal from the level control mechanism representing a specified electro-magnetic field strength set point;
- the control signal generator forming a signal to regulate the power flowing from the electrical power supply to the magnetic field coil;
- a controller responding to the signal from the control signal generator and providing an output voltage based on the magnitude of the signal from the control signal generator; and
- a rectifier converting the output voltage of the controller to direct current output power and providing the direct current output power to the magnetic field generating coil.

15. The magnetic field generator of claim 14, wherein the magnetic field generating coil generates a static magnetic field ranging in strength from 0 to 4,000 gauss based on the amount of power received.

16. The magnetic field generator of claim 14, wherein the field strength sensor is a Hall effect sensor.

* * * * *